United States Patent [19]

Kameswaran

[11] Patent Number: 5,225,568
[45] Date of Patent: Jul. 6, 1993

[54] PROCESS FOR THE PREPARATION OF INSECTICIDAL, ACARICIDAL AND NEMATICIDAL 2-ARYL-3-SUBSTITUTED-5-(TRI-FLUOROMETHYL)PYRROLE COMPOUNDS

[75] Inventor: Venkataraman Kameswaran, Princeton Junction, N.J.

[73] Assignee: American Cyanamid Company, Stamford, Conn.

[21] Appl. No.: 981,626

[22] Filed: Nov. 25, 1992

[51] Int. Cl.$^5$ .................. C07D 207/34; C07D 207/36; C07D 207/30
[52] U.S. Cl. .................. 548/531; 548/556; 548/557; 548/560; 558/308
[58] Field of Search ............... 548/531, 556, 557, 560; 558/308

[56] References Cited

U.S. PATENT DOCUMENTS

| | | | |
|---|---|---|---|
| 5,010,098 | 4/1991 | Brown et al. | 514/426 |
| 5,128,485 | 7/1992 | Kameswaran | 548/561 |

*Primary Examiner*—Mary C. Lee
*Assistant Examiner*—Joseph K. McKane
*Attorney, Agent, or Firm*—John W. Hogan, Jr.

[57] ABSTRACT

There is provided a process for the preparation of 2-aryl-3-substituted-5-(trifluoromethyl)pyrrole compounds which are useful as insecticidal, acaricidal and nematicidal agents.

8 Claims, No Drawings

PROCESS FOR THE PREPARATION OF INSECTICIDAL, ACARICIDAL AND NEMATICIDAL 2-ARYL-3-SUBSTITUTED-5-(TRIFLUOROMETHYL)PYRROLE COMPOUNDS

BACKGROUND OF THE INVENTION

Arylpyrrole compounds useful as insecticidal, acaricidal and nematicidal agents are described in U.S. Pat. No. 5,010,098. A method for the preparation of certain arylpyrrole compounds via the condensation of an enamine with an α-haloketone is described in U.S. Pat. No. 5,128,485. The method or U.S. Pat. No. 5,128,485 is useful for the preparation of said arylpyrrole compounds. However, arduous or time-consuming methods are required to prepare certain α-haloketones.

It is therefore an object of the present invention to provide a process for the preparation of insecticidal, acaricidal and nematicidal 2-aryl-3-substituted-5-(trifluoromethyl)pyrrole compounds which avoids the use of α-haloketones.

SUMMARY OF THE INVENTION

The present invention is directed to a process for the preparation of 2-aryl-3-substituted-5-(trifluoromethyl)pyrrole compounds of formula I (I)

wherein

A is hydrogen or $C_1$-$C_6$ alkyl optionally substituted with phenyl;

W is CN, $NO_2$, $CO_2R_1$ or $SO_2R_1$;

L is hydrogen, F, Cl, Br or I;

M and R are each independently hydrogen, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, CN, F, Cl, Br, I, $NO_2$, $CF_3$, $R_2CF_2Z$, or $NR_4R_5$ and when M and R are on adjacent positions they may be taken together with the carbon atoms to which they are attached to form a ring in which MR represents the structure —$OCH_2O$—, —$OCF_2O$— or —CH=CH—CH=CH—;

$R_1$ is $C_1$-$C_6$ alkyl, $C_3$-$C_6$ cycloalkyl or phenyl;

$R_2$ is hydrogen, F, $CHF_2$, CHFCl or $CF_3$;

$R_3$ is $C_1$-$C_4$ alkyl, $C_1$-$C_4$ alkoxy or $NR_4R_5$;

$R_4$ is hydrogen or $C_1$-$C_4$ alkyl;

$R_5$ is hydrogen, $C_1$-$C_4$ alkyl or $R_6CO$;

$R_6$ is hydrogen or $C_1$-$C_4$ alkyl;

Z is $S(O)_n$ or O; and n is an integer of 0, 1 or 2 which comprises reacting a haloenamine of formula II (II)

wherein X is Cl, Br or I, and A, W, L, M and R are as described above with about one molar equivalent of trifluoroacetone in the presence of an acid and optionally in the presence of a solvent.

The 2-aryl-3-substituted-5-(trifluoromethyl)pyrrole compounds of formula I are useful as insecticidal, acaricidal and nematicidal agents. Those compounds are also useful as intermediates in the preparation of certain arylpyrrole insecticidal, acaricidal and nematicidal agents. The utility of the formula I compounds is described in U.S. Pat. No. 5,010,098.

DETAILED DESCRIPTION OF THE INVENTION

Surprisingly, it has been found that insecticidal, acaricidal and nematicidal 2-aryl-3-substituted-5-(trifluoromethyl)pyrrole compounds of formula I may be prepared in a single step process by reacting a haloenamine of formula II with about one molar equivalent of trifluoroacetone in the presence of an acid and optionally in the presence of a solvent preferably at an elevated temperature. The above reaction is shown below in Flow Diagram I.

FLOW DIAGRAM I

A preferred process of the present invention comprises reacting a formula II compound wherein W is CN or $NO_2$; X is Cl, Br or I; A is hydrogen or methyl; L is hydrogen; M is hydrogen, F, Cl, Br or I; and R is F, Cl, Br, I, $CF_3$ or $OCF_3$ with about one molar equivalent of trifluoroacetone in the presence of an acid and optionally in the presence of a solvent preferably at an elevated temperature. By elevated temperature it is meant a temperature above room temperature (i.e. above about 20°–25° C.).

Acids suitable for use in the process of the present invention include organic acids such as acetic acid, propionic acid and the like with acetic acid being preferred. Solvents suitable for use in the present invention include organic solvents such as hydrocarbons, halogenated hydrocarbons, aromatic hydrocarbons and halogenated aromatic hydrocarbons having a boiling range of from about 70° C. to 250° C., such as benzene, toluene, xylene and the like. Reaction temperatures of about 70° C. to 150° C. are suitable, with 80° C. to 130° C. being preferred.

The product formula I compounds may be isolated by conventional techniques such as dilution of the reaction mixture with water and filtration of the formula I product or extraction of said product with a suitable solvent. In the isolation procedure any suitable extraction solvents may be employed, including water-immiscible solvents such as ether, ethyl acetate, toluene, methylene chloride and the like.

Compounds of formula II may be prepared by reacting the appropriate enamine of formula III with a halogenating agent such as a halogen, an N-halosuccinimide, a hypohalite or the like as shown in Flow Diagram II.

FLOW DIAGRAM II

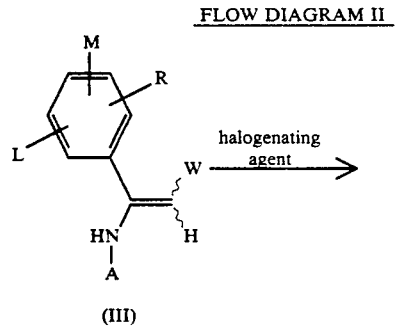

In order to facilitate a further understanding of the invention, the following examples are presented to illustrate more specific details thereof. The invention is not to be limited thereby except as defined in the claims.

EXAMPLE 1

Preparation of 2-(p-Chlorophenyl)-1-methyl-5-(trifluoromethyl)pyrrole-3-carbonitrile

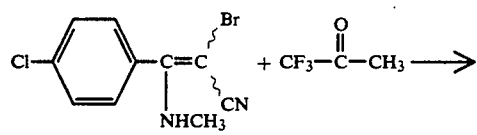

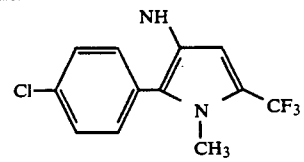

A solution of α-bromo-p-chloro-β-(methylamino)cinnamonitrile, (E)- or (Z)- (5.43 g, 0.02 mol) and trifluoroacetone (3.36 g, 2.7 mL, 0.03 mol) in acetic acid is heated at 80° C. for 1-2 hours, heated at 100° C. overnight, diluted with water and extracted with ethyl acetate. The combined organic extracts are washed with water, dried over anhydrous $Na_2SO_4$ and concentrated in vacuo to obtain a gum. The gum is flash chromatographed using silica gel and a 15% ethyl acetate in heptane solution to give the title product as a yellow solid (1.7 g, mp 129°-131° C.) which is identified by $^1H$ and $^{19}F$ NMR spectral analyses.

EXAMPLE 2

Preparation of 2-(p-Chlorophenyl)-5-(trifluoromethyl)pyrrole-3-carbonitrile

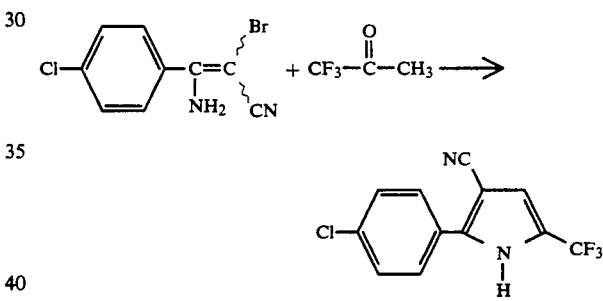

A solution of trifluoroacetone (3.36 g, 2.7 mL, 0.03 mol) in acetic acid is added dropwise at 100° C. to a solution of β-amino-α-bromo-p-chlorocinnamonitrile, (E)- or (Z)- (5.15 g, 0.02 mol) in acetic acid over 4½ hours. The reaction mixture is heated at 100° C. overnight, diluted with water and extracted with ethyl acetate. The combined organic extracts are washed with water, dried over anhydrous $Na_2SO_4$ and concentrated in vacuo to obtain a gum. The gum is flash chromatographed using silica gel and a 15% ethyl acetate in heptane solution to give the title product as a yellow solid (1.8 g, mp 129°-131° C.) which is identified by $^1H$ and $^{19}F$ NMR spectral analyses.

EXAMPLE 3

Preparation of α-Bromo-p-chloro-β-(methylamino)cinnamonitrile, (E)- or (Z)-

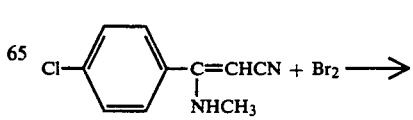

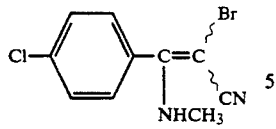

A solution of bromine (10.9 mL, 33.6 g, 0.21 mol) in carbon tetrachloride is added to a mixture of p-chloro-β-(methylamino)cinnamonitrile, (E)- or (Z)- (38.53 g, 0.2 mol) in carbon tetrachloride and tetrahydrofuran at 55°–60° C. over 30 minutes. The reaction mixture is cooled to room temperature, concentrated in vacuo to one-half of the original volume and filtered to obtain a solid. The solid is diluted with carbon tetrachloride and the resulting mixture is heated at reflux, cooled and filtered to give the title product as a yellow solid (43.6 g, mp 178°–178.5° C.) which is identified by $^1$H and $^{13}$CNMR spectral analyses.

Using essentially the same procedure, but substituting β-amino-p-chlorocinnamonitrile for p-chloro-β-(methylamino)cinnamonitrile, (E)- or (Z)-, β-amino-α-bromo-p-chlorocinnamonitrile, (E)- or (Z)- is obtained as a white solid, mp 190°–191.5° C.

I claim:

1. A process for the preparation of a 2-aryl-3-substituted-5-(trifluoromethyl)pyrrole compound of formula I

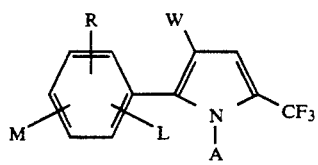

wherein

A is hydrogen or $C_1$–$C_6$ alkyl optionally substituted with phenyl;

W is CN, $NO_2$, $CO_2R_1$ or $SO_2R_1$;

L is hydrogen, F, Cl, Br or I;

M and R are each independently hydrogen, $C_1$–$C_4$ alkyl, $C_1$–$C_4$ alkoxy, $C_1$–$C_4$ alkylthio, $C_1$–$C_4$ alkylsulfinyl, $C_1$–$C_4$ alkylsulfonyl, CN, F, Cl, Br, I, $NO_2$, $CF_3$, $R_2CF_2Z$, $R_3CO$ or NR and when M and R are on adjacent positions they may be taken together with the carbon atoms to which they are attached to form a ring in which MR represents the structure —$OCH_2O$—, —$OCF_2O$— or
—CH=CH—CH=CH—;

$R_1$ is $C_1$–$C_6$ alkyl, $C_3$–$C_6$ cycloalkyl or phenyl;

$R_2$ is hydrogen, F, $CHF_2$, CHFCl or $CF_3$;

$R_3$ is $C_1$–$C_4$ alkyl, $C_1$–$C_4$ alkoxy or $NR_4R_5$;

$R_4$ is hydrogen or $C_1$–$C_4$ alkyl;

$R_5$ is hydrogen, $C_1$–$C_4$ alkyl or $R_6CO$;

$R_6$ is hydrogen or $C_1$–$C_4$ alkyl;

Z is $S(O)_n$ or O; and n is an integer of 0, 1 or 2 which comprises reacting a haloenamine of formula II

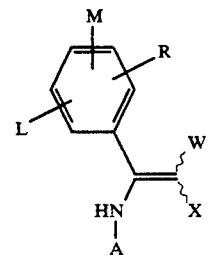

wherein X is Cl, Br or I, and A, W, L, M and R are as described above with about one molar equivalent of trifluoroacetone in the presence of an acid and optionally in the presence of a solvent to form said formula I compound.

2. The process according to claim 1 wherein the acid is acetic acid.

3. The process according to claim 1 wherein

A is hydrogen or methyl;

W is CN or $NO_2$;

L is hydrogen;

M is hydrogen, F, Cl, Br or I; and

R is F, Cl, Br, I, $CF_3$ or $OCF_3$.

4. The process according to claim 3 wherein

M is F, Cl, Br or I; and

R is F, Cl, Br or I.

5. The process according to claim 3 wherein

M is hydrogen; and

R is F, Cl, Br or I.

6. The process according to claim 1 wherein the reaction takes place at an elevated temperature.

7. The process according to claim 6 wherein the elevated temperature is about 70° C. to 150° C.

8. The process according to claim 7 wherein the elevated temperature is about 80° C. to 130° C.

* * * * *

UNITED STATES PATENT AND TRADEMARK OFFICE
CERTIFICATE OF CORRECTION

PATENT NO. : 5,225,568
DATED : July 6, 1993
INVENTOR(S) : Venkataraman Kameswaran It is certified that error appears in the above-indentified patent and that said Letters Patent is hereby corrected as shown below:

In Claim 1, Col. 5, line 45, "NR and" should be

-- $NR_4R_5$ and --.

Signed and Sealed this

Eighth Day of February, 1994

Attest:

BRUCE LEHMAN

Attesting Officer

Commissioner of Patents and Trademarks